(12) United States Patent
Hsieh et al.

(10) Patent No.: US 11,062,445 B2
(45) Date of Patent: Jul. 13, 2021

(54) METHOD OF MEDICAL IMAGE REGISTRATION

(71) Applicants: HIWIN TECHNOLOGIES CORP., Taichung (TW); China Medical University, Taichung (TW)

(72) Inventors: Bao-Yu Hsieh, Taichung (TW); Tzung-Chi Huang, Taichung (TW); Hsien-Te Chen, Taichung (TW); You-Min Chen, Taichung (TW); Yi-Cheng Liu, Taichung (TW)

(73) Assignees: HIWIN TECHNOLOGIES CORP., Taichung (TW); CHINA MEDICAL UNIVERSITY, Taichung (TW)

( * ) Notice: Subject to any disclaimer, the term of this patent is extended or adjusted under 35 U.S.C. 154(b) by 118 days.

(21) Appl. No.: 16/554,144

(22) Filed: Aug. 28, 2019

(65) Prior Publication Data

US 2021/0065359 A1 Mar. 4, 2021

(51) Int. Cl.
*G06K 9/00* (2006.01)
*G06T 7/00* (2017.01)
(Continued)

(52) U.S. Cl.
CPC ............ *G06T 7/0012* (2013.01); *A61B 6/032* (2013.01); *G06T 3/0068* (2013.01); *G06T 7/38* (2017.01);
(Continued)

(58) Field of Classification Search
CPC ................. G06T 7/0012; G06T 3/0068; G06T 2207/10081; G06T 7/38;
(Continued)

(56) References Cited

U.S. PATENT DOCUMENTS

2006/0241445 A1* 10/2006 Altmann ................... A61B 8/12
600/443
2008/0107312 A1* 5/2008 Von Berg .................. G06T 7/30
382/128
(Continued)

FOREIGN PATENT DOCUMENTS

CN 1853576 B 10/2011
CN 102232835 A1 11/2011
(Continued)

OTHER PUBLICATIONS

Taiwanese Search Report, dated Sep. 9, 2019, for Taiwanese Application No. 108109701, with an English translation.
(Continued)

*Primary Examiner* — Van D Huynh
(74) *Attorney, Agent, or Firm* — Birch, Stewart, Kolasch & Birch, LLP

(57) ABSTRACT

A method of medical image registration is to be implemented by a computer device, and includes steps of: obtaining an ultrasound target image corresponding to an area of interest in an ultrasound image; for each of multiple computed tomography (CT) images, obtaining a CT candidate image that corresponds to an area of interest in the CT image; for each of the CT candidate images, calculating a similarity between the CT candidate image and the ultrasound target image; making one of the CT candidate images that corresponds to the greatest similarity among the CT candidate images serve as a CT target image; and performing image registration on the ultrasound target image and the CT target image.

6 Claims, 10 Drawing Sheets

(51) Int. Cl.
*A61B 6/03* (2006.01)
*G06T 3/00* (2006.01)
*G06T 7/38* (2017.01)

(52) U.S. Cl.
CPC .............. *G06T 2207/10081* (2013.01); *G06T 2207/10088* (2013.01); *G06T 2207/10132* (2013.01)

(58) Field of Classification Search
CPC . G06T 2207/10088; G06T 2207/10132; A61B 6/032
USPC ......................................................... 382/128
See application file for complete search history.

(56) References Cited

U.S. PATENT DOCUMENTS

| | | | | |
|---|---|---|---|---|
| 2008/0177279 | A1* | 7/2008 | Sumanaweera | A61B 90/10 606/130 |
| 2011/0028844 | A1* | 2/2011 | Hyun | A61B 8/13 600/443 |
| 2011/0052030 | A1* | 3/2011 | Bruder | A61B 6/4014 382/131 |
| 2016/0125605 | A1* | 5/2016 | Lee | A61B 8/085 382/131 |
| 2016/0317129 | A1* | 11/2016 | Seip | A61B 8/483 |
| 2017/0340268 | A1* | 11/2017 | Danielsson | A61B 6/4241 |
| 2018/0098816 | A1* | 4/2018 | Govari | A61B 8/4254 |

FOREIGN PATENT DOCUMENTS

| | | |
|---|---|---|
| CN | 107595390 A | 1/2018 |
| EP | 1 720 038 A2 | 8/2006 |
| WO | WO 2005/083629 A1 | 9/2005 |

OTHER PUBLICATIONS

Beitzel et al., "Ultrasound Bone Detection Using Patient-Specific CT Prior". 34th Annual International Conference of the IEEE EMBS. Aug. 29, 2012, pp. 2664-2667.

Search Report appended to an Office Action, which was issued to Chinese counterpart application No. 201910303270.2 by the CNIPA dated Mar. 29, 2021, with an English translation thereof.

* cited by examiner

METHOD OF MEDICAL IMAGE REGISTRATION

FIELD

The disclosure relates to a method of image registration, and more particularly to a method of medical image registration.

BACKGROUND

Conventionally, a surgeon relies heavily on preoperative data, e.g., computed tomography (CT) images of a subject, in locating a site to be treated (also known as "surgical site") on the subject. However, when operating on the subject, slight movements of the subject caused by actions of the surgeon (e.g., forcing an intramedullary rod into the medullary cavity of a bone of the subject) may displace the surgical site relative to the surgical/operating table or other surgical equipment used during surgery, thereby adversely affecting accuracy of the operation in the process to follow.

In addition, while the surgeon still has to rely on CT images captured during the operation in order to track the surgical site, the surgeon is not instantly informed of the aforementioned displacement of the surgical site with the periodic, namely, non-continuous, CT scans. In addition, the repeated CT scans may expose the subject to a high dose of radiation. Therefore, a method to provide assistance to the surgeon to instantly track the surgical site during operation is demanded.

SUMMARY

Therefore, an object of the disclosure is to provide a method of medical image registration that can alleviate at least one of the drawbacks of the prior art.

According to the disclosure, the method of medical image registration is to be implemented by a computer device, and includes steps of:

(A) obtaining an ultrasound target image from an ultrasound image of one of multiple portions of a bone of a subject, the ultrasound target image corresponding to an area of interest in the ultrasound image;

(B) for each of multiple computed tomography (CT) images of respective portions of the bone of the subject, obtaining a CT candidate image that corresponds to an area of interest in the CT image;

(C) for each of the CT candidate images obtained for the CT images, calculating a similarity between the CT candidate image and the ultrasound target image;

(D) making one of the CT candidate images that corresponds to the greatest similarity among the CT candidate images serve as a CT target image; and (E) performing image registration on the ultrasound target image and the CT target image.

BRIEF DESCRIPTION OF THE DRAWINGS

Other features and advantages of the disclosure will become apparent in the following detailed description of the embodiments with reference to the accompanying drawings, of which:

FIGS. 5 and 6 cooperatively constitute a flowchart for illustrating another embodiment of the method of medical image registration according to the disclosure;

DETAILED DESCRIPTION

Figure 1:
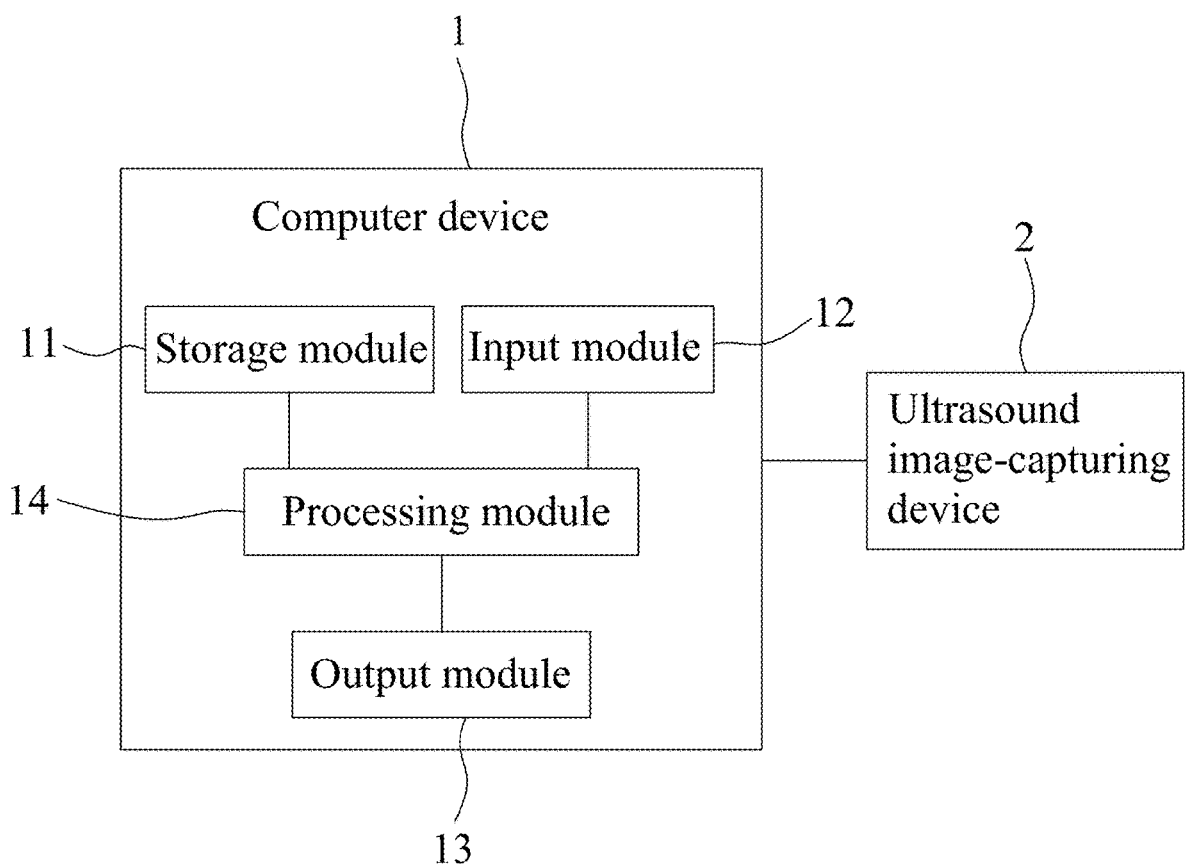
FIG. 1 is a block diagram illustrating an embodiment of a computer device to be utilized to implement a method of medical image registration according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Referring to FIG. 1, an embodiment of a computer device 1 that is utilized to implement a method of medical image registration is illustrated. The computer device 1 is electrically connected to an ultrasound image-capturing device 2. The method of medical image registration is adapted to spatially transform a computed tomography (CT) image of a portion of a bone of a subject (patient) to align with an ultrasound image of the corresponding portion of the bone of the subject.

The computer device 1 may be implemented by a personal computer, a computing server or a cloud server, but implementation of the computer device 1 is not limited to the disclosure herein and may vary in other embodiments. The computer device 1 includes a storage module 11, an input module 12, an output module 13, and a processing module 14 that is electrically connected to the storage module 11, the input module 12, and the output module 13.

In this embodiment, the storage module 11 may be implemented by a flash memory, a hard disk drive (HDD), a solid state disk (SSD), an electrically-erasable programmable read-only memory (EEPROM) or any other non-volatile memory devices, but implementation of the storage module 11 is not limited to the disclosure herein and may vary in other embodiments.

In this embodiment, the input module 12 may be implemented by a keyboard, a mouse or a touchpad, but implementation of the input module 12 is not limited to the disclosure herein and may vary in other embodiments.

In this embodiment, the output module 13 may be implemented by a display, a monitor or a printer, but implementation of the output module 13 is not limited to the disclosure herein and may vary in other embodiments.

In this embodiment, the processing module 14 may be implemented by a processor, a central processing unit (CPU), a microprocessor or any circuit configurable/programmable in a software manner and/or hardware manner to implement functionalities of this disclosure.

In this embodiment, the ultrasound image-capturing device 2 may be implemented to be an ultrasonic diagnostic apparatus available on the market, but implementation thereof is not limited to the disclosure herein and may vary in other embodiments.

Figure 2:
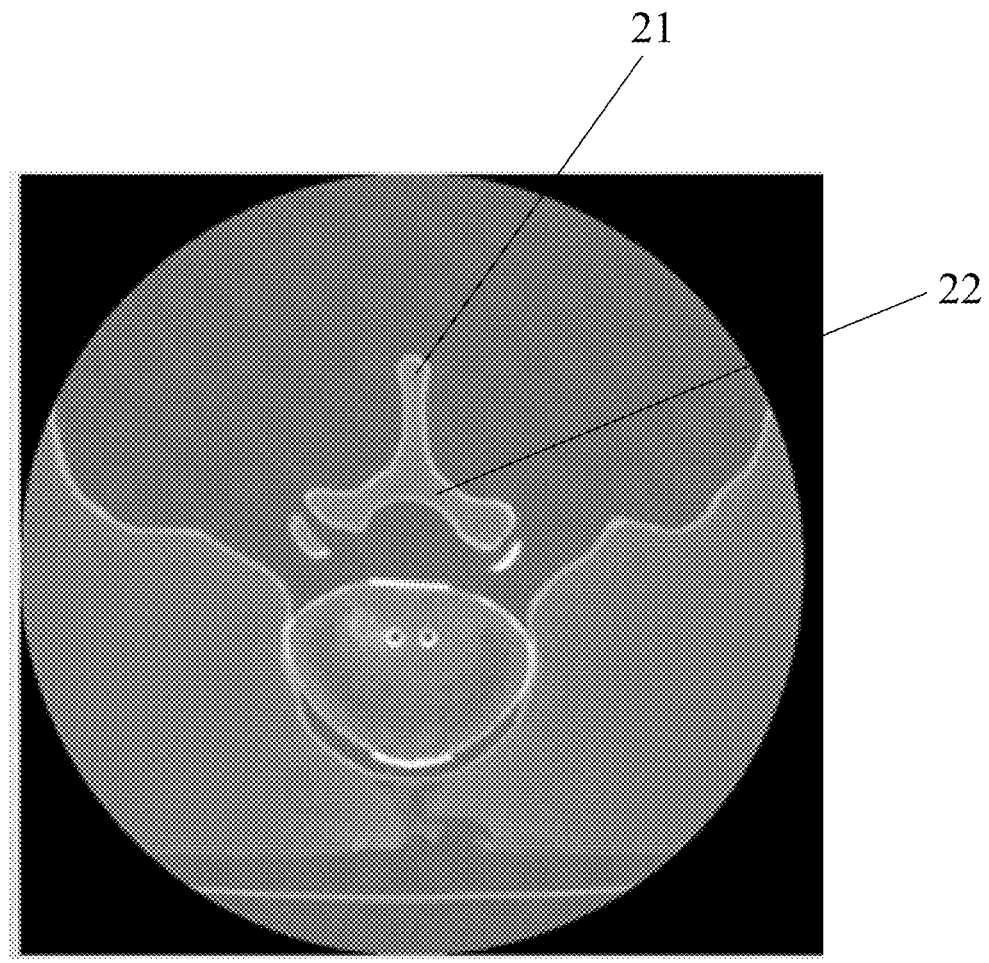
FIG. 2 is a schematic diagram illustrating an exemplary computed tomography (CT) image stored in the computer device.

The storage module 11 stores multiple CT images of respective portions of the bone of the subject. In this embodiment, the bone of the subject is a vertebral column. The vertebral column includes a plurality of vertebrae. Each of the CT images such as the one shown in FIG. 2 corresponds to a respective one of sections of one of the vertebrae. Each of the CT images is oriented such that a spinous process of the vertebra in the CT image is located at a relatively upper side of the CT image, as indicated by 21, and a lamina of the vertebra in the CT image is located at a relatively lower side of the CT image, as indicated by 22.

Figure 3:
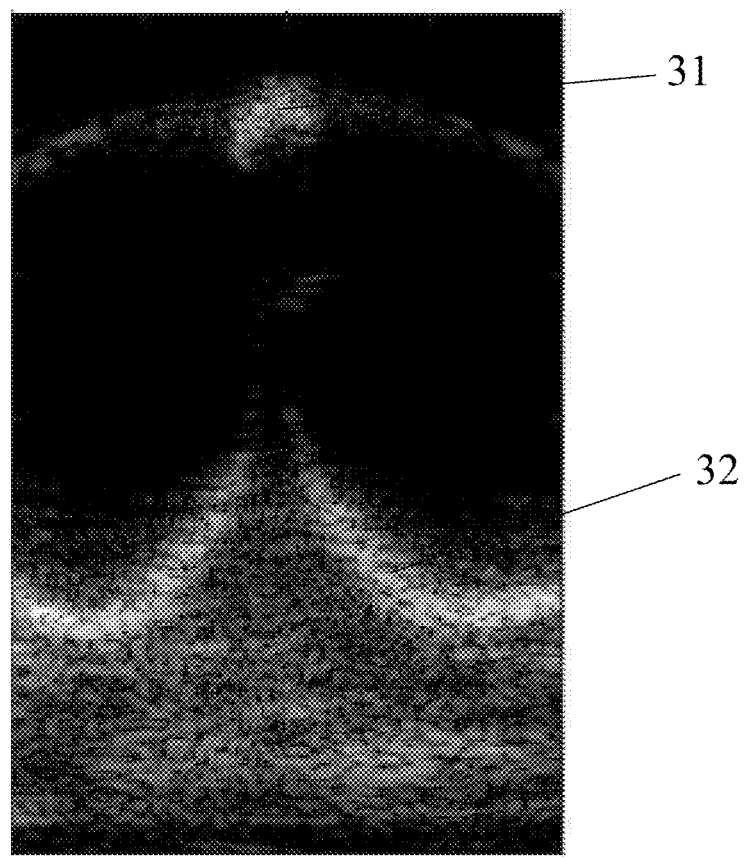
FIG. 3 is a schematic diagram illustrating an exemplary ultrasound image captured by an ultrasound image-capturing device.

The ultrasound image-capturing device 2 is configured to capture the ultrasound image of one of the portions of the bone of the subject, and to transmit the ultrasound image to the computer device 1. It is worth to note that the ultrasound image-capturing device 2 captures the ultrasound image of a section of one of the vertebrae of the subject as shown in FIG. 3 when the subject is in the prone posture. In this way, the spinous process of the vertebra in the ultrasound image is located at a relatively upper side of the ultrasound image, as indicated by 31, and the lamina of the vertebra in the ultrasound image is located at a relatively lower side of the ultrasound image, as indicated by 32. That is to way, the ultrasound image and the CT images are oriented in the same way.

Figure 4:
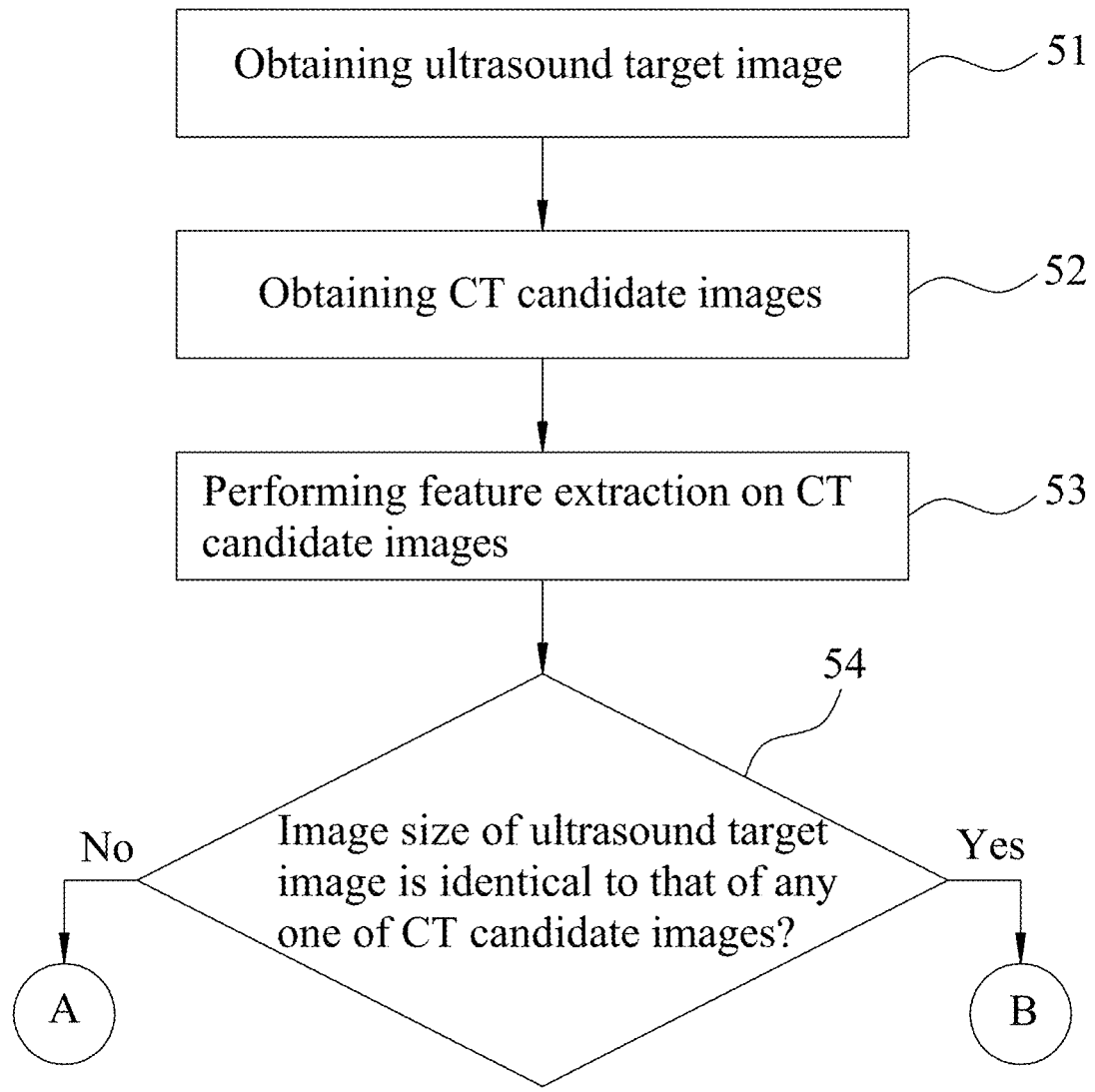
FIGS. 4 and 5 cooperatively constitute a flowchart for illustrating an embodiment of the method of medical image registration according to the disclosure.
Figure 5:
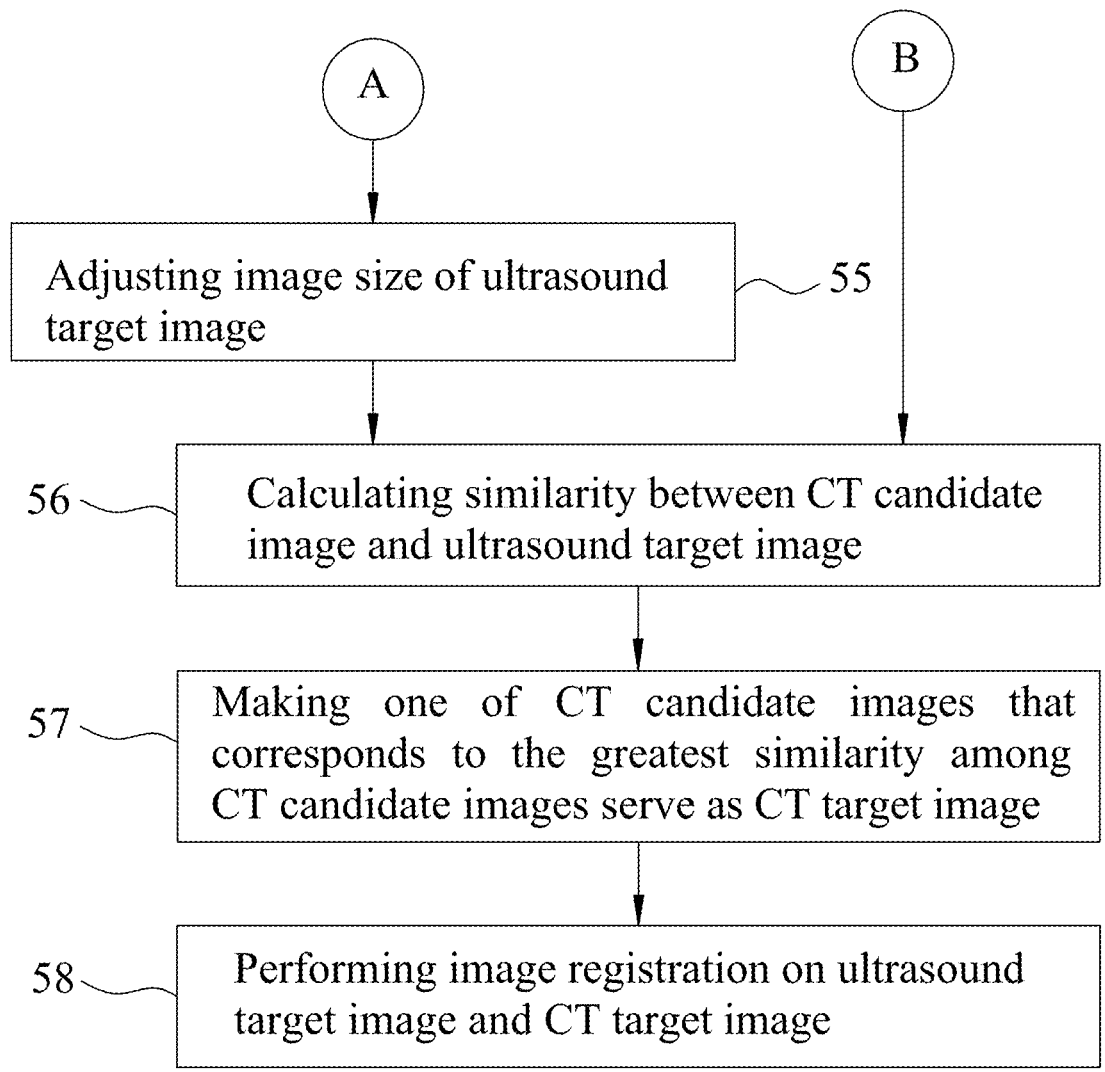

Referring to FIGS. 4 and 5, an embodiment of the method of medical image registration is illustrated. The method of medical image registration includes steps 51 to 58 described as follows.

Figure 7:
FIG. 7 is a schematic diagram illustrating an exemplary ultrasound target image that corresponds to the ultrasound image.

In step 51, in receipt of the ultrasound image, the computer device 1 obtains an ultrasound target image as shown in FIG. 7 from the ultrasound image, where the ultrasound target image corresponds to an area of interest in the ultrasound image. Specifically speaking, in response to an input operation of a surgeon via the input module 12, the computer device 1 generates an input signal, and obtains the ultrasound target image based on the ultrasound image and the input signal. For instance, the ultrasound target image is a section of the ultrasound image selected according to the input signal. However, in other embodiments, the computer device 1 may be implemented to obtain the ultrasound target image from the ultrasound image by means of image recognition techniques.

Figure 8:
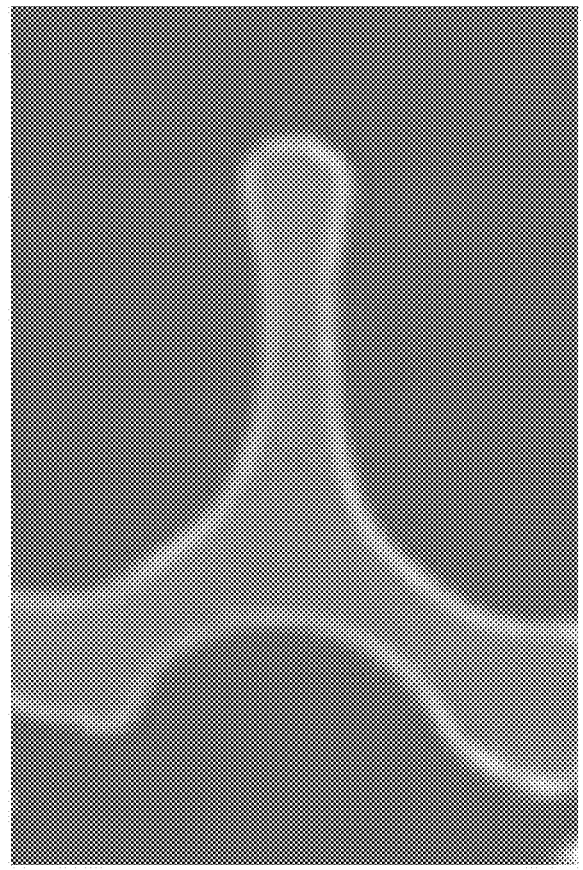
FIG. 8 is a schematic diagram illustrating an exemplary CT candidate image that corresponds to one of multiple CT images.

In step 52, for each of the CT images, the computer device 1 obtains a CT candidate image, such as an image shown in FIG. 8, from the CT image, where the CT candidate image corresponds to an area of interest in the CT image. Specifically speaking, for each of the CT images, in response to another input operation of the surgeon via the input module 12, the computer device 1 generates another input signal, and obtains the CT candidate image based on the CT image and said another input signal. For instance, the CT candidate image is a section of the corresponding CT image selected according to said another input signal. However, in other embodiments, the computer device 1 may be implemented to obtain the CT candidate image from the CT image by means of image recognition techniques.

Since the image recognition techniques have been well known to one skilled in the relevant art, detailed explanation of the same is omitted herein for the sake of brevity.

Figure 9:
FIG. 9 is a schematic diagram illustrating an embodiment of a exemplary CT candidate image that is post feature extraction, where the feature extraction is related to an upper contour of an object in the CT candidate image.

In step 53, for each of the CT candidate images, the computer device 1 performs feature extraction related to an upper contour of an object in the CT candidate image so that the CT candidate image only contains the upper contour of the object as shown in FIG. 9. Specifically speaking, for each of the CT candidate images, the computer device 1 removes noise from the CT candidate image, keeps an uppermost pixel that has a non-zero pixel value in each column of the CT candidate image, and changes all other pixels in the CT candidate image into pixels with zero pixel values, leaving the CT candidate image with only the extracted upper contour of the object. In one embodiment, the computer device 1 further changes each of the uppermost pixels thus kept to have a pixel value equal to 255 so that the extracted upper contour of the object has uniform pixel value.

Figure 6:
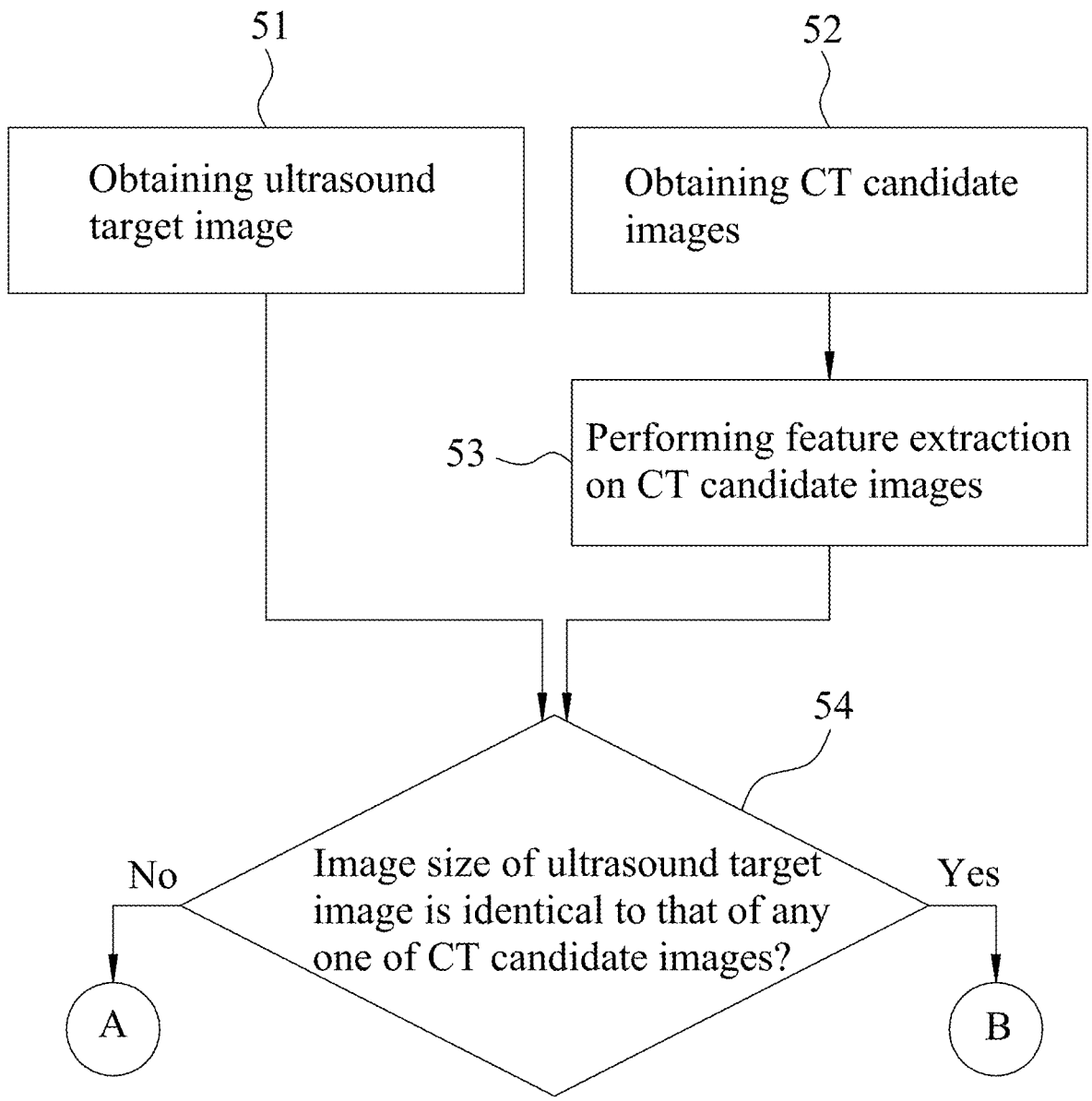

Referring to FIG. 6, it should be noted that in other embodiments, execution of steps 52 and 53 is in parallel to execution of step 51 so as to accelerate processing of the method of medical image registration.

It is worth noting that when the CT candidate image which only contains the extracted upper contour of the object is used for subsequent similarity analysis with the ultrasound target image, since portions other than the upper contour have been eliminated, these portions are prevented from interfering with the similarity analysis. In this way, compared with directly using the CT candidate image without feature extraction where the upper contour of the object is not singled out and extracted for the similarity analysis, quality of the similarity analysis is upgraded, and accuracy of image registration is thereby enhanced.

In step 54, the computer device 1 determines whether an image size of the ultrasound target image is identical to an image size of any one of the CT candidate images. When it is determined by the computer device 1 that the image size of the ultrasound target image is not identical to the image size of any one of the CT candidate images, a flow of procedure proceeds to step 55. Otherwise, the flow proceeds to step 56.

In step 55, based on the image size of an arbitrary one of the CT candidate images, the computer device 1 adjusts the image size of the ultrasound target image to be identical to the image size of the arbitrary one of the CT candidate images.

It should be noted that the adjustment of the image size of the ultrasound target image and the extraction of the upper contour of the object performed on each of the CT candidate images are not necessarily included in the method of medical image registration according to the disclosure, and may be omitted in other embodiments.

In step 56, for each of the CT candidate images (either with or without feature extraction), the computer device 1 calculates a similarity between the CT candidate image and the ultrasound target image (either with the original image size or the adjusted image size). Specifically speaking, for each of the CT candidate images, the computer device 1 calculates the similarity between the CT candidate image and the ultrasound target image according to mutual information (MI) therebetween, and calculates a parameter set of a geometric transformation related to a mapping relationship between the CT candidate image and the ultrasound target image according to the MI therebetween. In other embodiments, the computer device 1 calculates the similarity between the CT candidate image and the ultrasound target image based on an iterative closest points (ICP) algorithm.

In step 57, the computer device 1 makes one of the CT candidate images that corresponds to the greatest similarity among the CT candidate images serve as a CT target image.

Figure 10:
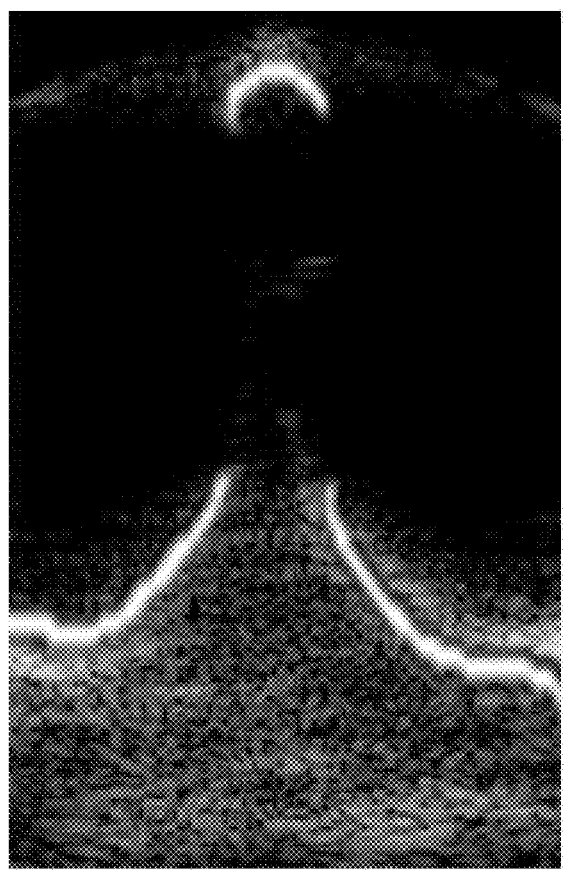
FIG. 10 is a schematic diagram illustrating an exemplary result of image registration on the ultrasound target image and the CT target image.

In step 58, the computer device 1 performs image registration on the ultrasound target image and the CT target image, and provides a result (see FIG. 10) of the image registration in a visual presentation via the output module 13 (e.g., displayed on a display) to serve as a reference for a surgeon to instantly track a site to be treated on the subject (patient) during an operation. Specifically speaking, the computer device 1 performs image registration on the ultrasound target image and the CT target image based on the parameter set of the geometric transformation that corresponds to the ultrasound target image and the CT target image. In other embodiments, the computer device 1 performs image registration on the ultrasound target image and the CT target image based on a B-spline algorithm.

To sum up, the method of medical image registration according to this disclosure utilizes the computer device 1 to calculate, for each of the CT candidate images, the similarity between the CT candidate image and the ultrasound target image based on the MI therebetween, to obtain the CT target image which is one of the CT candidate images that corresponds to the greatest similarity among the CT candidate images, and to perform image registration on the ultrasound target image and the CT target image. Consequently, the method of medical image registration according to the disclosure facilitates the surgeon to instantly track the site to be treated on the subject (patient) during the operation, alleviating the problem of excessive radiation absorption by the subject.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. A method of medical image registration, the method to be implemented by a computer device and comprising:
    (A) obtaining an ultrasound target image from an ultrasound image of one of multiple portions of a bone of a subject, the ultrasound target image corresponding to an area of interest in the ultrasound image;
    (B) for each of multiple computed tomography, CT, images of respective portions of the bone of the subject, obtaining a CT candidate image that corresponds to an area of interest in the CT image;
    (C) for each of the CT candidate images obtained for the CT images, calculating a similarity between the CT candidate image and the ultrasound target image;
    (D) making one of the CT candidate images that corresponds to the greatest similarity among the CT candidate images serve as a CT target image; and
    (E) performing image registration on the ultrasound target image and the CT target image,
    between steps (B) and (C), the method further comprising:
    (H) for each of the CT candidate images, performing feature extraction related to an upper contour of an object in the CT candidate image so that the CT candidate image only contains the upper contour of the object.

2. The method as claimed in claim 1, between steps (B) and (C), further comprising:
    (F) determining whether an image size of the ultrasound target image is identical to an image size of any one of the CT candidate images; and
    (G) when it is determined that the image size of the ultrasound target image is not identical to the image size of any one of the CT candidate images, adjusting, based on the image size of an arbitrary one of the CT candidate images, the image size of the ultrasound target image to be identical to the image size of the arbitrary one of the CT candidate images.

3. The method as claimed in claim 1, wherein step (H) includes, for each of the CT candidate images, keeping an uppermost pixel that has a non-zero pixel value in each column of the CT candidate image, and changing all other pixels in the CT candidate image into pixels having zero pixel values, leaving the CT candidate image with only the upper contour of the object thus extracted.

4. The method as claimed in claim 3, wherein step (H) includes changing each of the uppermost pixels thus kept to have a pixel value equal to 255.

5. The method as claimed in claim 1, wherein step (C) includes calculating the similarity between the CT candidate image and the ultrasound target image according to mutual information (MI) therebetween.

6. The method as claimed in claim 5, wherein:
    step (C) further includes, for each of the CT candidate images, calculating a parameter set of a geometric transformation related to a mapping relationship between the CT candidate image and the ultrasound target image according to the MI therebetween; and
    step (E) includes performing image registration on the ultrasound target image and the CT target image based on the parameter set of the geometric transformation that corresponds to the ultrasound target image and the CT target image.

* * * * *